United States Patent [19]
Hartman et al.

[11] Patent Number: 5,866,778
[45] Date of Patent: Feb. 2, 1999

[54] NEWLY CHARACTERIZED OXALATE AND USES THEREFOR

[75] Inventors: Christina L. Hartman, Princeton, N.J.; Sarjit S. Johal, Newtown, Pa.; Mark R. Schmitt, Trenton, N.J.

[73] Assignee: Zeneca Limited, London, England

[21] Appl. No.: 272,514

[22] Filed: Jul. 11, 1994

Related U.S. Application Data

[60] Continuation of Ser. No. 061,801, May 17, 1993, abandoned, which is a division of Ser. No. 659,434, Feb. 25, 1991, abandoned.

[51] Int. Cl.$^6$ .............................. A01H 5/00; C12N 15/09; C12N 15/29; C12N 5/04
[52] U.S. Cl. ........................ 800/205; 800/200; 800/250; 800/255; 800/DIG. 14; 800/DIG. 17; 800/DIG. 52; 435/172.1; 435/172.3; 435/418; 435/419; 536/23.2; 536/23.6
[58] Field of Search .............................. 435/172.1, 172.3, 435/240.1, 240.4, 240.49, 240.5, 418, 419; 536/23.2, 23.6; 800/200, 205, 250, 255, DIG. 14, 17, 52; 935/67

[56] References Cited

U.S. PATENT DOCUMENTS

| | | | |
|---|---|---|---|
| 4,143,486 | 3/1979 | Maan | 47/58 |
| 4,956,282 | 9/1990 | Goodman et al. | 435/69.51 |

FOREIGN PATENT DOCUMENTS

| | | |
|---|---|---|
| WO88 08450 | 11/1988 | WIPO . |
| WO92 15685 | 9/1992 | WIPO . |

OTHER PUBLICATIONS

Dratweka–Kos et al, "Polypeptide Structure of Germin as Deduced from cDNA Sequencing", Journal of Biological Chemistry, vol. 264, No. 9, 25 Mar. 1989, pp. 4896–4900.
Schmitt et al, "Barley Seeding Oxlate Oxidase Purification and Properties", Supplement to Plant Physiology, vol. 96, No. 1, 1991.
Pietta et al, "Improved Purification Protocol for Oxalate Oxidase form Barley Roots", Chemical Abstracts, vol. 98, 1983, No. 13533.
Koyama, "Purification and Characterization of Oxalate Oxidase form Pseudomonas sp. OX–53", Agricultural and Biological Chemistry, vol. 52, No. 3, 1988, pp. 743–748.
Linthurst, H.J.M. et al, 1989, The Plant Cell, vol. 1, pp. 286–291.
Ahokas, H., Theor. Appl. Genet., vol. 77 (1989) pp. 469–472.
Dratewka–Kos, E. et al, 1989 J. Biol. Chem., vol. 264, pp. 4896–4900.
Grzelczak, Z.F., et al, 1985, Can J. Biochem. Cell. Biol., vol. 63, pp. 1003–1013.
Chiriboga, J., 1966, Arch. Biochem. Biophys., vol. 116, pp. 516–523.
Sugiura, M., et al, 1979, Chem. Pharm. Bull., vo.. 27, pp. 2003–2007.
Pietta, P.G. et al, 1982, Prep. Biochem., vol. 12, pp. 341–353.
Young, R.A., et al, 1983, Proc. Natl. Acad. Sci. USA, vol. 80, pp. 1194–1198.
Grzelczak, Z.F., et al, 1982, Can. J. Biochem., vol. 60, pp. 389–397.
Grzelczak, Z.F., et al, 1983, Can. J. Biochem. Cell. Biol., vol. 61, pp. 1233–1243.
Grzelczak, Z.F., et al, 1984, Can J. Biochem. Cell Biol., vol. 62, pp. 1351–1353.
Koleosho, B. et al 1987 Phytoparasitica vol. 15, pp. 317–323.
Libert, B. 1987, J. Horticult. Sci. vol. 62, pp. 523–529.
Noyes, R.D. et al, 1981, Biol. Abstr. vol. 72, Abs. 26852.
Horner, H.T. 1987, Am. J. Botany, vol. 74, p. 616.
Lane, B.G. et al, 1993, J. Biol. Chem. vol. 268, pp. 12239–12242.
Godoy, G. et al, 1990, Physiol. Molec. Plant. Pathol. vol. 37, pp. 179–191.
Zeddies, J. et al, 1984, Biol. Abstr. vol. 77, Abs. 48368.
Dumas et al. Tissue–specific expression of germin–like oxalate oxidase during development and fungal infection of barley seedings. Plant Physiology. 107:1091–1096 1995.
Thompson et al. Degradation of oxalic acid by transgenic oilseed rape plants expressing oxalate oxidase. Euphytica. 85:169–172 1995.
Zhang et al. Germin–like oxalate oxidase, a $H_2O_2$–producing enzyme, accumulates in barley attacked by the powdery mildew fungus. The Plant Journal. 81:139–145 1995.
Potrykus. 1991. Annu. Rev. Plant Physiol. Plant Mol. Biol. 42:205–225.
Finnegar et al. 1994. Bio/Technology. 12:883–888.
Weising et al. 1988. Annu. Rev. Genet. 22:421–477.
Lane, 1988. In The Roots of Modern Biochemistry. von Klein Kauf et al., eds. pp. 457–476.

*Primary Examiner*—Douglas W. Robinson
*Assistant Examiner*—Melissa L. Kimball
*Attorney, Agent, or Firm*—Cushman Darby Cushman IP Group of Pillsbury Madison & Sutro LLP

[57] ABSTRACT

This invention pertains to methods for using oxalate oxidase in plant pathology. A substantially pure gene encoding the oxalate oxidase enzyme is elucidated. The expression product of the gene which can be stably incorporated into a foreign plant host has a unique profile including a pH optimum of 3.5, a positive heat stability, a single sub-unit of approximately 25 kilodaltons and protease stability. The methodology of this invention exploiting oxalate oxidase for protection against oxalic acid encompasses providing to a plant in need of oxalic acid protection an oxalic acid degrading enzyme in an amount sufficient to protect the plant from the oxalic acid.

19 Claims, 3 Drawing Sheets

Fig. 1

SEQ. ID NO.

1  NNNGACCCAG ACCCACTCCA GGACTTCTGC GTCGCGGACC TCGATGGCAA
   GGCGGTCTCG GTGAACGGGC ATACGTGTAA GCCCATGTCG GAGGCCGGCG
   ACGACTTCCT CTTCTCGTCC AAGCTGACCA AGGCCGGCAA CACGTCCACC
   CCGAACGGCT CGG

2  G GAGCTCGACG TGGCCGAGTG GCCGGTACGA    ACACGCTGGG

3                          AACCGTGTGG ACTTCGCGCC GGGCGGCACC
   AACCCGCCGC ACATCCACCC GCGTGCAACC GAGATCGGCA TGGTGATGAA
   AGGTGAGCTC CTCGTTGGAA TCCTCGGCAG CCTTGACTCC GGAAACAAGC
   TCTACTCCAG GGTGGTGCGT GCCGGAGAGA CTTTCGTCAT CCCGCGCGGC
   CTCATGCACT TCCAGTTCAA CGTTGGTAAG ACGGAAGCCT ACATGGTTGT
   GTCCTTCAAC AGCCAGAACC CTGGCATCGT CTTCGTGCCG CTCACACTCT
   TCGGCTCCGA CCCTCCCATC CCCACGCCCG TGCTCACCAA GGCTCTCCGG
   GTGGAGGCCG GAGTCGTGGA ACTTCTCAAG TCCAAGTTCG CCGGTGGGTC
   TTAACTTCCA TGAGCCCCAA ATGATCAATA TGAATATGTA ATTCTATATA
   TCCATGTATG CTGCGAATTT AATAGTACTC GACAGGAGAC TATACCGGAA
   TTC

Fig. 2

```
            3              6              9             12  13
Ser-Asp-Pro-Asp-Pro-Leu-Gln-Asp-Phe-Cys-Val-Ala-Asp-Leu-
          16         18
Asp-Gly-Lys-Ala
```

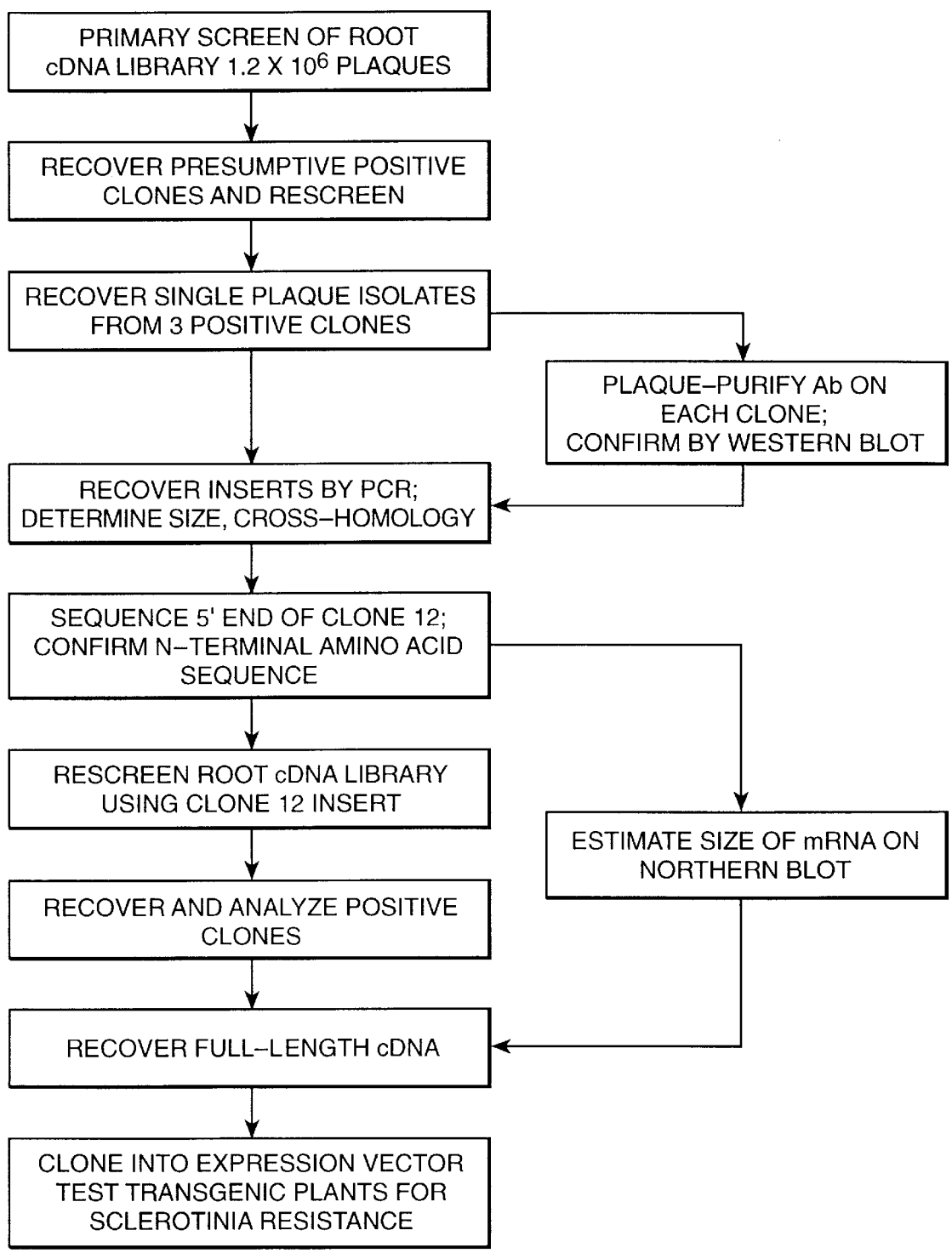

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 163 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
NNNGACCCAG  ACCCACTCCA  GGACTTCTGC  GTCGCGGACC  TCGATGGCAA  GGCGGTCTCG      60
GTGAACGGGC  ATACGTGTAA  GCCCATGTCG  GAGGCCGGCG  ACGACTTCCT  CTTCTCGTC      120
AAGCTGACCA  AGGCCGGCAA  CACGTCCACC  CCGAACGGCT  CGG                        163
```

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGAGCTCGAC  GTGGCCGAGT  GGCCGGTACG  AACACGCTGG  G                          41
```

( 2 ) INFORMATION FOR SEQ ID NO:3:

( i ) SEQUENCE CHARACTERISTICS:
        ( A ) LENGTH: 483 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AACCGTGTGG  ACTTCGCGCC  GGGCGGCACC  AACCCGCCGC  ACATCCACCC  GCGTGCAACC     60
GAGATCGGCA  TGGTGATGAA  AGGTGAGCTC  CTCGTTGGAA  TCCTCGGCAG  CCTTGACTC     120
GGAAACAAGC  TCTACTCCAG  GGTGGTGCGT  GCCGGAGAGA  CTTTCGTCAT  CCCGCGCGG    180
CTCATGCACT  TCCAGTTCAA  CGTTGGTAAG  ACGGAAGCCT  ACATGGTTGT  GTCCTTCAA    240
AGCCAGAACC  CTGGCATCGT  CTTCGTGCCG  CTCACACTCT  TCGGCTCCGA  CCCTCCCAT    300
CCCACGCCCG  TGCTCACCAA  GGCTCTCCGG  GTGGAGGCCG  GAGTCGTGGA  ACTTCTCAA    360
TCCAAGTTCG  CCGGTGGGTC  TTAACTTCCA  TGAGCCCCAA  ATGATCAATA  TGAATATGT    420
ATTCTATATA  TCCATGTATG  CTGCGAATTT  AATAGTACTC  GACAGGAGAC  TATACCGGA    480
TTC                                                                       483
```

( 2 ) INFORMATION FOR SEQ ID NO:4:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

```
Ser  Asp  Pro  Asp  Pro  Leu  Gln  Asp  Phe  Cys  Val  Ala  Asp  Leu  Asp  Gly
1                    5                        10                        15
Lys  Ala
```

NEWLY CHARACTERIZED OXALATE AND USES THEREFOR

This is continuation of application Ser. No. 08/061,801, filed on May 17, 1993, which was abandoned upon the filing hereon, which is a divisional of application Ser. No. 07/659,434 filed Feb. 25, 1991 now abandoned.

FIELD OF THE INVENTION

This invention relates to plant biology. Specifically, this invention relates to the field of plant disease. More specifically, the invention relates to prevention of plant disease.

BACKGROUND OF THE INVENTION

From the beginning of agriculture humans have been confronted with the problem of plant disease. Throughout history many strides have been made against plant diseases as exemplified through the use of hybrid plants, pesticides and improved agricultural practices. However, as any farmer, home gardener, or houseplant devotee can attest, the problems of plant disease are an ongoing and constant problem in plant cultivation. This invention constitutes a major step forward in solving the problem of plant disease by exploiting a long known fact regarding the method by which certain microbes, especially fungi, attack plants. Specifically, this invention addresses a means by which the etiologic (disease causing) agent is slowed or prevented from actually entering into the plant tissue, thereby preventing disease. Alternatively, in instances where complete invasion is not prevented the present invention confers upon plants a means for reducing the effects of infection thereby reducing or preventing plant mortality due to the disease.

In order for a plant pathogen to infect a plant, it must be able to gain access into and subsequently throughout the plant. Plant pathogens accomplish this in various ways. Generally, this is accomplished by the secretion of chemical substances that affect certain component and/or metabolic mechanisms of the plant to be attacked, i.e. the host for the pathogen. The main groups of compounds that are secreted by plant pathogens and that are related to the disease-causing mechanism are toxins, enzymes, polysaccharides and/or other effectors of growth. One such chemical compound is oxalic acid or oxalate which can be degraded by the enzyme oxalate oxidase. Although the reaction catalyzed by oxalate oxidase is well-known, the physico-chemical attributes of the enzyme as exemplified by barley oxalate oxidase are incorrectly reported in the literature. The secretion of oxalic acid as a means by which plant pathogens attack plant hosts is commonly found in a plurality of fungal genera and especially in the genera Sclerotinia, Sclerotium, Aspergillus, Streptomyces, Penicillium, Pythium, Paxillus, Mycena, Leucostoma, Rhizoctonia and Schizophyllum. These genera of fungi, especially those fungi of the genus Sclerotinia, are known to cause destructive and fatal diseases of numerous highly cultivated plants including field crops such as sunflower, soybean, beans in general, rape/canola, alfalfa, flax, safflower, peanut and clover, vegetable crops such as lettuce, tomato, cucurbits, potato, carrot, radish, pea, lentils, cabbage, broccoli and brussel sprouts, flowers such as petunia and pyrethrum and tree species such as peach. The diseases include not only pre-harvest diseases in the field but also post-harvest diseases during shipping and storage.

The symptoms caused by the aforementioned fungal genera vary with the host plant and the parts of the host plant infected with the disease, as well as being dependant upon environmental conditions at the time of pathogen attack. For example, a feature of all Sclerotinia disease is wilting and collapse of the leaves whereupon the fungus rapidly invades the "heart" of the plant and throughout the stem. The disease is fatal.

In liquid cultures of Sclerotinia levels of oxalic acid ranging from a thousand to ten thousand parts per million, depending upon growth media, age of the culture and other parameters have been observed. Certain plant tissue such as leaves of bean and sunflower exposed to low concentrations of oxalic acid readily show signs of wilting and cell death suggesting the importance of oxalic acid in later stages of disease. The precise mechanism of the disease causing function of oxalic acid after infection is unknown although theories range from chelation of divalent metals interfering with plant cell walls and/or key metabolic enzymes to providing an optimum micro-environment for the action of hydrolytic enzymes secreted by these fungi. Regardless, it is clear from extant evidence that oxalic acid is an integral component of pathogenic attack. Evidence for this conclusion has been obtained by several studies including investigations with oxalate-minus Sclerotinia mutants that appear to possess the normal complement of hydrolytic enzymes and other factors but do not produce disease symtomology. Revertants of these oxalate minus mutants demonstrated normal disease development and characteristics.

The high degree of virulence of diseases associated with the aforementioned fungal genera are well-known. For example, leaves of greenhouse grown sunflower plants infected with *Sclerotinia sclerotiorum* frequently exhibit wilting and interveinal necrosis three to five days after inoculation. Study of these plants has shown a wilt inducing substance in water extracts of hypocotyl (the part of the axis of a plant embryo or seedling below the cotyledon) lesions. Chemical tests including thin layer chromatography and gas-liquid chromatography have demonstrated that this wilt inducing substance contained oxalic acid and that wilted leaves from infected plants contained over fifteen times more oxalic acid than leaves of healthy plants. As already noted, the oxalic acid moves systemically through the plant to cause disease symptoms in tissues that are both distant from the initial point of infection and not necessarily infected with fungal hyphae.

With this backdrop, the inventors realized that appropriate identification, isolation and expression of an oxalate degrading enzyme such as an oxalate oxidase, oxalate decarboxylase or similar enzyme by a plant might well diminish the pathogenicity of fungi which secrete oxalic acid as a key component of pathogenicity. Accordingly, the inventors set out and achieved the goal of properly identifying and isolating a gene for a protein that is suitable for the introduction of oxalate oxidase activity into plants and microbes using the techniques of genetic engineering.

In particular, the inventors have characterized an enzyme useful in thwarting pathogenicity involving oxalic acid. This uniquely characterized oxalate oxidase enzyme catalyzes or otherwise contributes to a reaction involving the oxidative degradation of oxalate to produce carbon dioxide and hydrogen peroxide. The general form of this reaction is: oxalate+ $O_2$ oxalate/oxidase$\rightarrow 2CO_2 + H_2O_2$. The study of this enzyme has resulted not only in its identification, isolation and expression, but also in its characterization and its cloning so that a gene for expression of the enzyme is extant, can be introduced into plants, and expressed by plants thereby conferring disease resistance to fungi in which oxalic acid is a critical component. Such plant transformation would protect the transformed plants against the deleterious disease causing effects of oxalic acid.

It will be appreciated that the applications of the aforementioned inventions are not limited to plant pathogenesis. Still another benefit of this invention is the introduction of an oxalate oxidase gene into a plant to produce a low oxalic acid plant. This could be especially beneficial in high oxalate plants such as peanuts, beets, spinach, rhubarb, barley, cocoa, and many grasses. See, Libert and Franceschi (1987), J. Agric. Food Chem., 35:926–938. Also, the invention has application for the large scale production of oxalate degrading enzymes. The need for such large scale oxalate degrading enzymes is known in a variety of fields including the need for their use in assay kits to determine the presence and/or amount of oxalic acid and for use in the degradation of oxalic acid present in foodstuffs, beverages and commercial processes. For example, a microbial oxalate decarboxylase has been used by the brewing industry (U.S. Pat. No. 4,652,452) and as set forth herein oxalate can also be degraded using oxalate oxidase.

It is, therefore, an object of this invention to fully purify and properly characterize an oxalate oxidase.

It is another object of this invention to isolate, characterize and construct a gene which can express oxalate oxidase in microbes and plants.

It is a further object of this invention to introduce an oxalate oxidase expressing gene into plants thereby conferring on such plants resistance to diseases, especially fungal diseases in which oxalic acid is a major component such as in diseases of the fungal genera Sclerotinia, Sclerotium, Aspergillus, Streptomyces, Penicillium, Pythium, Paxillus, Mycena, Leucostoma, Rhizoctonia and Schizophyllum.

SUMMARY OF THE INVENTION

The present invention is broadly directed to the understanding and appreciation of the use of an oxalate degrading enzyme as exemplified by oxalate oxidase for commercial uses such as in the brewing industry or for agronomic uses such as to reduce susceptibility of a plant to oxalic acid or to reduce the endogenous oxalic acid concentration in a plant. The inventors have come to appreciate and teach herein, particularly for agronomic application, the use of oxalate degrading enzymes to reduce plant mortality or destruction from diseases or other phenomenon in which oxalic acid plays a critical invasive role. The inventors have also appreciated that use of this invention can result in the prevention of plant mortality and infection from diseases in which oxalic acid is critical. Such diseases are particularly caused by, among others, the specific genera of fungi set forth herein.

The appreciation of the inventor's novel uses of oxalate degrading enzymes is especially enhanced by the realization and invention of the inventors that the physico-chemical properties of barley oxalate oxidase as reported in the literature was inaccurate. Accordingly, the inventors have substantially purified and characterized an oxalate oxidase enzyme not heretofore described. Indeed, the purported substantial purifications of the enzyme as set forth in the literature are shown herein to be incorrect. Specifically, the inventors disclose a substantially pure oxalate oxidase having a particular total amino acid composition, particular N-terminal amino acid sequence excepting the first residue thereof which is believed to be serine, a pH optimum of 3.5, a neutral isoelectric point, a positive heat stability, protease stability and a single subunit of approximately 25 kilodaltons.

Also set forth herein is the invention of substantially all of a substantially pure gene encoding an oxalate oxidase enzyme with a specific DNA sequence as shown in FIG. 1 and having the structure of (SEQ ID NO. 1) . . . (SEQ ID NO. 2) . . . (SEQ ID NO. 3) . . . wherein ". . ." represents a gap or region of unknown sequence. The gene encodes the oxalate oxidase enzyme having the characteristics as set forth above. In particular the gene encodes an enzyme exhibiting oxalate oxidase activity having a single subunit of approximately 25 kilodaltons, that reacts specifically with antibodies raised against purified barley oxalate oxidase, and has an amino acid sequence shown in FIG. 2 (SEQ ID NO:4).

The invention also discloses compounds for use in combatting plant pathogenesis which compounds include chemicals exhibiting oxalic acid degrading activity in particular oxalate oxidase activity. Specifically, the plant compound has oxalate oxidase activity in an amount sufficient to break down oxalic acid produced by pathogens. It will be appreciated that another agronomic use for such a compound is to combine the compounds with an appropriate carrier, which is agronomically acceptable, permitting delivery of the compound directly to the plant or to the soil.

A transformed plant cell is also disclosed herein, which cell is transformed by a gene encoding the expression of oxalate oxidase or another oxalate degrading enzyme. The gene encoding such enzyme can include the DNA sequence set forth in FIG. 1 having the structure (SEQ ID NO. 1) . . . (SEQ ID NO. 2) . . . (SEQ ID NO. 3) . . . which substantially corresponds to the oxalate oxidase enzyme substantially purified by the inventors.

A method is disclosed herein for providing protection against oxalic acid to a plant in need of protection from such oxalic acid. The method includes providing an oxalic acid degrading enzyme in an amount sufficient to protect the plant from the oxalic acid to a plant in need of such protection. Preferably, it is envisioned that the oxalic acid degrading enzyme is oxalate oxidase encoded by a gene having the structure (SEQ ID NO. 1) . . . (SEQ ID NO. 2) . . . (SEQ ID NO. 3) . . . The methodology for providing such protection can take a plurality of forms including the transformation of a plant with a gene encoding an oxalic acid degrading enzyme and in particular encoding oxalate oxidase. Alternatively, the method can include provision of an oxalic acid degrading enzyme in combination with an agronomically acceptable carrier for direct application to a plant or to soil in which the plant grows.

BRIEF DESCRIPTION OF THE FIGURES

FIG. 1 shows a partial but substantially complete DNA sequence reverse engineered from the mRNA coding for barley seedling oxalate oxidase.

FIG. 2 shows the amino terminus amino acid sequence of oxalate oxidase purified from barley root seedling. The serine at position one has not been verified.

FIG. 4 shows diagrammatically the cloning strategy adopted and effectuated to clone the oxalate oxidase gene.

DETAILED DESCRIPTION OF THE INVENTION

Figure 3:
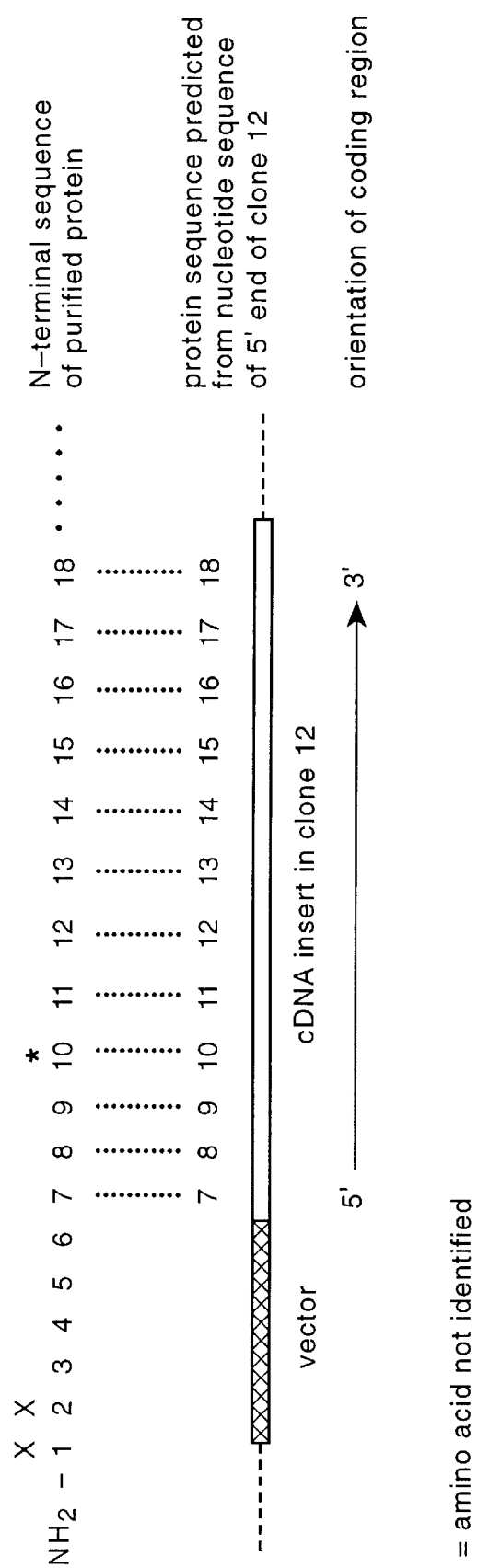
FIG. 3 shows a comparison of the partial protein sequence of purified oxalate oxidase and nucleotide sequence of cDNA clone 12.

The purified oxalate oxidase of this invention, its use as an agent to fight pathogenesis and its use in plant cell transformation provide an innovative and unique approach to the control of plant diseases in which oxalic acid plays a critical component either during pathogenesis or at the invasive stage. It is, of course, well-known that the activity of the enzyme oxalate oxidase is that it contributes to the degradation of oxalic acid. However, it was the current inventors who first appreciated that by attacking the oxalic acid by chemical degradation, for example by enzymatic degradation, a significant agricultural benefit in conferring disease resistance against those diseases in which oxalic acid plays a critical role would result. This invention holds special promise because a major scourge in the commercial cultivation of agronomically important plants, for example crops such as sunflowers, is caused by fungal species such as Sclerotinia that secrete oxalic acid.

The benefits of the inventor's insight can be exploited either by plant transformation or by application of oxalate oxidase as a traditional pesticide most probably in combination with a suitable carrier that is agriculturally acceptable. One of the important benefits of the use of oxalate oxidase as a pesticide is that it is ecologically sound, non-polluting and does not harm the plant.

If an external application of the enzyme is to be used to protect a plant or plant part against pathogens, it would be expected that the enzyme would be diluted to form a liquid solution or suspension or mixed with a diluent solid to be applied as a dust. The precise nature of application will depend in part on the particular pathogens) and plant(s) targeted. Detailed methods for adapting general methods of application to specific crops and pathogens can be found in "Methods for evaluating pesticides for control of plant pathogens", K. D. Hickey, ed., The American Phytopathological Society, 1986. Adjuncts that could be added to the formulation include agents to aid solubilization, wetting agents and stabilizers, or agents that would produce a microencapsulated product. Such adjuncts are well-known in the art.

External applications could also utilize recombinant microorganisms in either a viable form or after being converted into a non-viable form by a method that does not inactivate the enzyme.

Although the prior art reportedly purified oxalate oxidase and characterized it, the inventors have discovered that such literature reports were inaccurate and that the enzyme was, in fact, never properly purified and characterized. It will be appreciated that as used herein, "oxalate oxidase" refers to the purified and characterized form of the enzyme as set forth herein unless stated otherwise. The differences between the extant literature reports and the purified and characterized enzyme of the current invention are set forth in detail herein and can be briefly gleaned from Table 1.

The impurity of commercially available oxalate oxidase preparations as well as the improper characterization of the enzyme in the literature was evident when the inventors first purified oxalate oxidase from barley seedling root. Two procedures were used. In one instance purification of the barley seedling root oxalate oxidase involved homogenization of frozen tissue in 1 to 4 volumes of water and purification from the aqueous extract following filtration through cheesecloth to remove debris. The solution was further purified by centrifugation at 18,000 g for 30 minutes followed by heat treatment at 80° C. for 3 minutes with the precipitates at both steps being discarded; protein precipitating from the supernatant between 30% and 70% saturation with respect to ammonium sulfate $(NH_4)_2SO_4$ was collected by centrifugation and was dialyzed against water.

Protein resolubilizing from the ammonium sulfate precipitation step was fractionated on a Pharmacia FPLC using a Mono S 10/10 column equilibrated with 25 mM potassium acetate pH 4.8 eluted with a 0.0 to 0.4M NaCl gradient in the same buffer. Oxalate oxidase activity was measured by the method of Sugiura, et al. (1979), Chem. Pharm. Bull. 27(9):2003. Peak fractions of oxalate oxidase activity were combined, equilibrated with the low salt potassium acetate pH 4.8 buffer and rechromatographed on the FPLC using a Mono S 5/5 column eluted with the buffers and NaCl gradient as above. Peak fractions from the Mono S 5/5 step were combined, equilibrated with 25 mM Tris-Cl, pH 7.6 applied to a Mono Q 5/5 column and eluted with a 0.0 to 0.4M NaCl gradient. Sodium dodecyl sulfate polyacrylamide gel electrophoresis of peak oxalate oxidase activity fractions showed prominent protein bands upon silver staining at approximately 25 and 38–40 kilodaltons.

Subsequent size fractionation of the native protein on a Superose-12 gel filtration column (equilibrated with 50 mM potassium acetate, pH 4.8) on the FPLC showed a well-defined peak of activity eluting at a time corresponding with the molecular weight of about 25,000. No oxalate oxidase activity was found eluting in any other fractions associated with other molecular weights.

A second method involved the use of detergent extraction. Four to seven day old barley seedling roots were powdered in the presence of liquid nitrogen and stored at −80° C. Storage under these conditions resulted in no apparent loss of activity. The stored tissue was homogenized with distilled water containing 0.5% taurodeoxycholate sodium salt, filtered and centrifuged. Oxalate oxidase assays on the two fractions (supernatant and pellet) reveal that both fractions possessed activity. Accordingly, the pellet was extracted with distilled water containing 0.5% taurodeoxycholate. Following exhaustive dialysis against distilled water, ammonium sulfate was added to concentrate and fractionate the soluble supernatant proteins. The precipitated proteins (30–70% ammonium sulfate fractions) were then resuspended in a small volume of distilled water containing detergent and desalted on a small gel permeation column (Sephadex G 25). The active fraction was applied to an anion exchange column (DEAE) using a Tris-HCl, pH 7.5 buffer and elution of bound protein effected using a sodium chloride gradient. The enzymatically active fraction was concentrated, desalted and then applied to a Mono-Q column (Pharmacia). A sodium chloride gradient was again employed to elute the proteins. Activity assays showed that the oxalate oxidase was concentrated in 3 fractions. Upon analysis of these fractions by SDS polyacrylamide gel electrophoresis, the activity was determined to be associated with a polypeptide of about kilodalton molecular weight.

Following purification, characterization of the purified, homogeneous oxalate oxidase preparation was effectuated. As already indicated and as shown in Table 1 the properties of the protein resulting from this purification plainly differ from that described in the literature. This suggests that despite attempts by others skilled in the art to purify the oxalate oxidase enzyme, it was not until the present efforts of the inventors that this enzyme was properly described and fingerprinted through the elucidation of its physico-chemical properties. The results of the physico-chemical characterization undertaken by the inventors are set forth in Table 1. By way of comparison, the previously reported literature characterization of the enzyme is also set forth.

TABLE 1

OXALATE OXIDASE PROPERTIES

| Property | Literature | Invention |
| --- | --- | --- |
| pH Opt. | 3.5 | 3.5 |
| Heat Stab. | + | + |
| Subunit No. | 2 | 1 |
| Size | 75k | 25k |
| pI | 2.8 | approx. 7 |
| Cofactors | − | − |
| Protease Stab. | unknown | + |
| Memb. Assoc. | unclear | + |

Further establishing the distinctiveness of the inventors' enzyme exhibiting oxalate oxidase activity can be seen in Table 2. As Table 2 plainly evidences this invention establishes an amino acid composition different than reported in the literature. See, Chiriboga, J. (1966) Archives of Biochemistry and Biophysics 116, 516–523.

TABLE 2

| Amino Acid | Invention | Literature |
| --- | --- | --- |
| Asx | 12.53 | 8.44 |
| Ser | 8.65 | 6.50 |
| Gly | 13.31 | 10.75 |
| Glx | 7.42 | 6.80 |
| Thr | 8.10 | 5.18 |
| Ala | 7.93 | 7.85 |
| Val | 8.41 | 6.40 |
| Met | 2.85 | 0 |
| Tyr | .98 | .93 |
| Ile | 2.15 | 6.39 |
| Leu | 9.36 | — |
| Phe | 6.89 | — |
| His | 1.79 | 1.68 |
| Lys | 5.98 | 4.90 |
| Trp | — | — |
| Arg | 3.65 | 3.48 |

Partially purified barley seed root oxalate oxidase was solubilized, subjected to cation exchange chromatography using a Mono S column (25 mM potassium acetate, pH 4.8, and eluted with a 0 to 400 millimolar potassium chloride gradient in the same buffer). The recovered enzymatically active protein was further purified by preparative sodium dodecyl sulfate polyacrylamide gel electrophoresis. A single protein band of about 25 kilodalton molecular weight band was detected and subsequently sliced from the gel.

The wet gel slices were fragmented, mixed with Freund's adjuvant and injected intramuscularly into the rear of the thigh muscle near the hip of the rabbits. The rabbits were boosted with additional quantities of protein and sample bleeds monitored to assure the production of oxalate oxidase specific antibodies. After about four months the animals were exsanguinated. The polyclonal rabbit antibodies produced were of very high titer.

The gene encoding for barley-derived oxalate oxidase having the structure (SEQ ID NO. 1) . . . (SEQ ID NO. 2) . . . (SEQ ID NO. 3) . . . , was cloned as shown in FIG. 4 using a cDNA library constructed from barley root. Total RNA was prepared from barley root. Polyadenylated RNA was then recovered from total RNA and used for the synthesis of cDNA. Both total and polyadenylated RNA were prepared using commercially available RNA extraction and mRNA purification kits according to the standard instructions provided with the kits (Pharmacia LKB Biotechnology Inc.). Construction of the library was commercially performed (Clontech Laboratories). The vector chosen for the library was lambda gt22. Use of this expression vector was selected based on the high titer and specificity of the oxalate oxidase antiserum. Whatever the expression vector selected for use with this conversion, it is advantageous for the vector to permit the use of an immunological screen for the protein product of oxalate oxidase cDNA clones. Based on the average insert size of 1.8 kilobases for the CDNA library and good representation as far as number of independent clones ($1.7 \times 10^6$), it was deduced that the library should contain a cDNA clone for the oxalate oxidase protein approximately 25 kilodaltons in size.

The initial screen of the library was performed with antiserum to oxalate oxidase according to standard procedures as, for example, set forth in Huynh, T., et al., (1985) *DNA Cloning Techniques: A Practical Approach,* D. Glover, ed. IRL Press, Oxford. Since information on the N-terminal amino acid sequence of the mature oxalate oxidase protein had been obtained (except for the N-terminal residue), the N-terminal sequence was also used to confirm the identity of any cDNA clones recovered as positive in the initial immunological screen. $1.2 \times 10^6$ plaques from the cDNA library were screened with the antiserum. Fourteen potentially positive signals were obtained one of which was much stronger than the others. Two sequential rounds of rescreening with the antiserum were performed on these fourteen clones in order to obtain confirmed positive, single plaque isolates which could be characterized at the molecular level. Plaque number 12 again gave the strongest signal throughout these subsequent screens. Plaque number 12 was then used to purify the oxalate oxidase antibody as a test of the specificity of the plaque signal, according to the standard procedure as described, for example, in Hunyh, T. et al., supra. Antibody purified from plaque 12 was used as a probe on a Western blot of an acrylamide gel of oxalate oxidase protein. The plaque-purified antibody reacted specifically with oxalate oxidase, showing a pattern identical to that seen with purified antibody as a probe.

The insert (CDNA product cloned into the vector lambda gt22) from plaque 12 was recovered using standard polymerase chain reaction (PCR) methods as exemplified in Ausubel, F. M. et al., eds., (1988) "The Polymerase Chain Reaction," in *Current Protocols in Molecular Biology,* Greene Publishing Associates and Wiley Interscience, New York, pp. 15.0.1–15.4.6. The insert in plaque number 12 was estimated to be 650–750 base pairs. The size of the insert in plaque 12 was consistent with a protein of about 25 kd. Based on the initial size estimate for the cDNA insert and the result from plaque purification of the antibody, plaque number 12 was considered to be the best candidate for further molecular analysis. The number 12 insert prepared by PCR was then recloned into a plasmid vector more amenable to analysis. The cDNA insert from clone 12 was also used as a probe to a Northern blot of barley root RNA to estimate the size of the mRNA for oxalate oxidase. Formaldehyde gel electrophoresis and transfer to a nylon membrane were carried out according to the procedures recommended by the commercial supplier of the membranes, Schleicher and Schuell. The number 12 probe hybridized to a single mRNA species approximately 800–850 bases long.

Dideoxy nucleotide sequencing was performed on the recloned plaque 12 insert. A commercially available T7 sequencing kit (Pharmacia LKB Biotechnology Inc.) and the manufacturer's recommended procedure were used. The barley cDNA insert was determined to be approximately 690 bases long with some uncertainty in two small regions covering no more than ten base pairs each, the C terminus and the identity of the three N terminal bases. The nucleotide sequence of the clone 12 insert is shown schematically in FIG. 1. The partial protein sequence was then predicted from the nucleotide sequence of clone 12 and compared to the N-terminal amino acid sequence obtained directly from the purified oxalate oxidase. This comparison is shown in FIG. 3.

The gene having the structure (SEQ ID No. 1) . . . (SEQ ID NO. 2) . . . (SEQ ID NO. 3) . . . containing the coding sequence for the mature oxalate oxidase enzyme would be attached to genetic regulatory elements which are needed for the expression of the structural gene in a defined host cell. The first type of regulatory element required is a gene promoter region, which contains DNA sequences recognized by the biological machinery of the plant cell and which induces transcription of the DNA sequence into messenger RNA (mRNA). The mRNA is then translated into the protein product coded for by the structural gene region. The promoter is attached in front of or 5' to the gene for oxalate oxidase, which can be performed according to standard methods known in the art. See, for example, T Maniatis, et al., (1982) Molecular Cloning, Cold Spring Harbor Laboratory, New York, pp. 104–106. Promoter regions which could be used for expression of the oxalate oxidase gene in plant cells include promoters which are active in a wide range of different plant tissues. For example, the 35S promoter from the cauliflower mosaic virus may be suitable for this purpose. Another type of promoter that could be used in plant cells is one which expresses under more restricted conditions. Included in this class would be promoters active only in certain tissue(s) of the plant and/or induced to be active by certain stimuli like wounding. An example of this kind of promoter would be the 5' regulatory region from the gene for phenylalanine ammonia lyase (PAL). This type of promoter is discussed in Liang, X. et al., (1989), PNAS, USA, 86:9284–9288. Expression of the oxalate oxidase gene in microbial hosts could be achieved by use of promoters obtained from microbial sources. Examples of such promoters would include the trp promoter for expression in bacteria such as *E. coli* as exemplified in Amann, E., et al., (1983) *Gene,* 25:167–178, or the glyceraldehyde phosphate dehydrogenase (GAPD) promoter for expression in yeast as exemplified in Edens, L. et al, (1984), "Synthesis and Processing of the Plant Protein Thaumatin in Yeast," *Cell* 37:629–633. The gene promoter sequences may also be derived in part or in whole from promoter sequences found in cells unlike those of the host cell as long as they meet the above criteria for transcription and translation.

A second genetic regulatory element which desirably could be, but need not be, attached to the oxalate oxidase gene is a terminator or polyadenylation sequence which promotes effective termination of transcription of the gene and, in eukaryotes, also promotes polyadenylation, i.e., the addition of any number of adenosine nucleotides at the 3' end of the mRNA. Standard methods known in the art can be used to attach the terminator region behind or 3' to the gene. (See, for example, T. Maniatis, et al., supra, pp. 104–106). An example of such a terminator/polyadenylation sequence for expression in plants would be that from the octopine synthase gene from an *Agrobacterium tumefaciens* Ti plasmid as enunciated in H. DeGreve et al., (1982), "Nucleotide sequence and transcript map of the *Agrobacterium tumefaciens* Ti plasmid-encoded octopine synthase gene,", J. Mol. Appl. Genet., 1:499–511. An example of such a terminator for expression in microbial hosts is the rho-independent transcription terminator sequence from *Salmonella typhimurium.* See, for example, M. E. Winkler, (1987), "*Escherichia coli* and *Salmonella typhimurium: Cellular and Molecular Biology*", F. C. Neidhardt, ed.-in-chief; American Society for Microbiology. The gene terminator sequences may also be derived in part or in whole from terminator sequences found in cells unlike those of the host cell, as long as they meet the above criteria for transcription termination and polyadenylation required by the host cell.

Another type of regulatory element which may be attached to the gene for oxalate oxidase is a DNA sequence coding for a signal peptide. The signal peptide is attached to the amino terminus of the protein and permits the protein to be localized to the cell wall or secreted from the host cell. During this localization process, the signal peptide is cleaved off, producing a protein product with the sequence of the mature protein. The DNA sequence for the signal peptide is inserted between the promoter and the coding region. Standard methods known in the art may be used to attach the DNA sequence for the signal peptide (See, for example, Maniatis, T., et al., supra, pp. 104–106). Examples of such signal sequences would include the signal peptide from an extensin gene of plants (Chen, J. and Varner, J. E., an extracellular matrix protein in plants: characterization of a genomic clone for carrot extensin." *EMBO J* 4:2145–2151, 1985) from the bacterial pelB (pectate lyase) gene of Erwinia carotovora (Lei, S. P. et al., (1987), J. Bacteriol. 169 4379) and from prepro factor of yeast (Smith, R. A., et al., Science 229:1219–1229, 1985). The signal peptide sequences may also be derived in whole or in part from terminator sequences found in cells unlike those of the host cell, as long as they meet the above criteria for processing and localization of the protein in the host cell.

Any of the various methods known for introducing foreign genes into plants could be used for insertion of the oxalate oxidase gene into a host plant. The methodology chosen to accomplish plant transformation with the oxalate oxidase gene would vary depending on the host plant. By way of example, one well-characterized methodology that would be useful for plant transformation with the oxalate oxidase gene would be Agrobacterium mediated transformation.

Agrobacterium mediated transformation using the oxalic oxidase gene follows the procedures well-known for this methodology. First, a gene cassette suitable for expression in plants is introduced into a disarmed strain of *Agrobacterium tumefaciens* as an intermediate host. The oxalate oxidase gene cassette is introduced into the T-DNA region of a recombinant plasmid containing a selectable marker gene such as a gene encoding for neomycin phosphotransferese II, phosphinothricin acetyl transferease or the like. This methodology is set forth in many literature publications including Horsch, et al., (1985), "A Simple and General Method for Transferring Genes Into Plants", Science, 227:1229–1231. Pieces of plant tissue, e.g. leaf, cotyledon or hypocotyl are co-incubated with the bacteria for 2–3 days before the bacteria are killed using antibiotics such as carbenicillin. Additional antibiotics corresponding to the selectable marker gene employed are included in the plant tissue culture medium such that only transformed plant cells will grow.

Plants regenerated from the transformed cells are then tested for the presence and expression of the oxalate oxidase gene. Amino assays and test for oxalate oxidase activity can be used to identify individual transformants. Tolerance to exogenous oxalic acid can also be used as a functional test of intact tissues.

As noted, several other methodologies are available for plant transformation apart from Agrobacterium transformation. Examples of these other DNA delivery methods include electroporation, i.e. chemically induced delivery into protoplasts, micro-injection, biolistics as well as others. An example of a types of plant that is not especially suitable for Agrobacterium-mediated transformation are soybean and certain cereals including maize. These plants would plainly benefit from plant transformation attempts using methodologies other than Agrobacterium-mediated transformation.

---

What is claimed is:

1. A method for the reduction of oxalate content in a plant tissue comprising stably incorporating into the genome of the plant a gene construct comprising a coding region encoding a subunit of a plant enzyme, said enzyme having oxalate oxidase activity, said subunit comprising the amino acid sequence of position 7 through position 18 of SEQ ID NO:4, and a promoter operably linked to and controlling expression of said coding region in said tissue.

2. A method as claimed in claim 1 in which said subunit of a plant enzyme is encoded by a barley gene.

3. A method as claimed in claim 1 in which said gene construct comprises a nucleotide sequence encoding a signal peptide operably linked to said subunit of a plant enzyme.

4. A method of combating plant pathogenesis by a pathogen which secretes oxalic acid, comprising stably incorporating into the genome of said plant by transformation a gene construct comprising a coding region encoding a subunit of a plant enzyme said enzyme having oxalate oxidase activity, said subunit comprising the amino acid sequence of position 7 through position 18 SEQ ID NO:4, and a promoter operably linked to and controlling expression of said coding region in said plant.

5. A method as claimed in claim 4 in which the said pathogen is a fungus of a genus selected from the group of oxalic acid secreting fungi consisting of Sclerotinia, Sclerotium, Aspergillus, Streptomyces, Penicillium, Pythium, Paxillus, Mycena, Leucostoma, Rhizoctonia, and Schizophyllum.

6. A method as claimed in claim 4 in which the plant is sunflower.

7. A method as claimed in claim 4 in which the plant is Oilseed Mape Orcanola.

8. A plant having stably incorporated within its genome by transformation a gene construct comprising a coding region encoding a subunit of a plant enzyme, said enzyme having oxalate oxidase activity, said subunit comprising the amino acid sequence of position 7 through position 18 of SEQ ID NO:4, and a promoter operably linked to and controlling expression of said gene in the tissue.

9. A method of degrading oxalate in plant tissue comprising: preparing a culture of cells of the plant; introducing into the cultured cells a gene construct comprising a gene promoter sequence capable of driving expression of a coding region in plant cells, a coding region operatively linked to the said promoter and encoding a subunit of a plant enzyme, said enzyme having oxalate oxidase activity, said subunit comprising the amino acid sequence of position 7 through position 18 of SEQ ID NO:4, and a 3'-untranslated region containing a polyadenylation signal; isolating from the culture those cells which have the construct in the genome; regenerating whole plants from the isolated cells; and selecting individuals expressing the oxalate-oxidase enzyme.

10. A method as claimed in claim 5 in which the fungus is *Sclerotinia sclerotiorum*.

11. A method as claimed in claim 4 in which said subunit of a plant enzyme is encoded by a barley gene.

12. A method as claimed in claim 11 wherein said coding region comprises the DNA sequences of SEQ ID NO: 1, SEQ TD NO:2 and SEQ ID NO:3.

13. A plant as claimed in claim 8 in which said subunit of a plant enzyme is encoded by a barley gene.

14. A plant as claimed in claim 13 wherein said coding region comprises the DNA sequences of SEQ ID NO: 1, SEQ ID NO:2 and SEQ ID NO:3.

15. A method as claimed in claim 9 in which said plant enzyme subunit is encoded by a barley gene.

16. A method as claimed in claim 15 wherein said coding region comprises the DNA sequences of SEQ ID NO: 1, SEQ ID NO:2 and SEQ ID NO 3.

17. A transformed plant cell having stably incorporated into its genome a gene construct comprising a coding region encoding a subunit of a plant enzyme, said enzyme having oxalate oxidase activity, said subunit comprising the amino acid sequence of position 7 through position 18 of SEQ ID NO:4, and a promoter operably linked to and controlling expression of said coding region in said tissue.

18. A plant cell as claimed in claim 17 in which said plant enzyme subunit is encoded by a barley gene.

19. A plant cell as claimed in claim 18 wherein said coding region comprises the DNA sequences of SEQ ID NO: 1, SEQ ID NO:2 and SEQ ID NO: 3.

* * * * *